(12) United States Patent
Schäfer et al.

(10) Patent No.: US 8,765,186 B2
(45) Date of Patent: *Jul. 1, 2014

(54) PROCESS FOR THE MANUFACTURE OF A POWDER CONTAINING CAROTENOIDS

(75) Inventors: Christian Schäfer, Rheinfelden (DE); David Schaffner, Rheinfelden (CH)

(73) Assignee: DSM IP Assets B.V., Heerlen (NL)

( * ) Notice: Subject to any disclaimer, the term of this patent is extended or adjusted under 35 U.S.C. 154(b) by 402 days.

This patent is subject to a terminal disclaimer.

(21) Appl. No.: 12/528,841

(22) PCT Filed: Mar. 4, 2008

(86) PCT No.: PCT/EP2008/001690
§ 371 (c)(1),
(2), (4) Date: Nov. 12, 2009

(87) PCT Pub. No.: WO2008/107152
PCT Pub. Date: Sep. 12, 2008

(65) Prior Publication Data
US 2010/0069510 A1    Mar. 18, 2010

(30) Foreign Application Priority Data
Mar. 5, 2007 (EP) .................................. 07004472

(51) Int. Cl.
*A23L 1/275* (2006.01)
*A61K 9/14* (2006.01)
*A23L 1/00* (2006.01)

(52) U.S. Cl.
CPC ............... *A23L 1/2753* (2013.01); *A61K 9/146* (2013.01); *A23L 1/0041* (2013.01); *A61K 2201/021* (2013.01)
USPC ........................................... 424/493; 426/540

(58) Field of Classification Search
None
See application file for complete search history.

(56) References Cited

U.S. PATENT DOCUMENTS

| 3,316,101 A | 4/1967 | Borenstein et al. |
| 6,162,474 A | 12/2000 | Chen et al. |
| 6,296,877 B1 | 10/2001 | Auweter et al. |

FOREIGN PATENT DOCUMENTS

| EP | 0 937 412 | 8/1999 |
| EP | 1 460 060 | 9/2004 |
| WO | WO 03/022071 | 3/2003 |
| WO | WO 2006/053761 | 5/2006 |
| WO | WO 2006053761 A2 * | 5/2006 |
| WO | WO 2007/009601 | 1/2007 |
| WO | WO 2007/090614 | 8/2007 |

* cited by examiner

*Primary Examiner* — H. Sarah Park
(74) *Attorney, Agent, or Firm* — Nixon & Vanderhye P.C.

(57) ABSTRACT

The present invention relates to a process for the manufacture of an emulsion or dispersion containing one or more carotenoids, in a preferred embodiment it relates to the manufacture of a powder containing one or more carotenoids, furthermore to the powder obtainable by said process and a food composition, especially a beverage, containing said powder.

7 Claims, 9 Drawing Sheets

PROCESS FOR THE MANUFACTURE OF A POWDER CONTAINING CAROTENOIDS

This application is the U.S. national phase of International Application No. PCT/EP2008/001690 filed 4 Mar. 2008 which designated the U.S. and claims priority to European Patent Application No. 07004472.2 filed 5 Mar. 2007, the entire contents of each of which are hereby incorporated by reference.

The present invention relates to a process for the manufacture of an emulsion or dispersion containing one or more carotenoids, in a preferred embodiment it relates to the manufacture of a powder containing one or more carotenoids, furthermore to the powder obtainable by said process and a food composition, especially a beverage, containing said powder.

Carotenoids are a particularly useful source of coloring agents for a variety of foods and beverages. The carotenoids include carotene, lycopene, bixin, zeaxanthin, cryptoxanthin, canthaxanthin, lutein, beta-apo-8'-carotenal, beta-apo-12'-carotenal and can provide color pigments ranging from yellow to red. An especially important member of the carotenoid class is beta-carotene, because beta-carotene is not only useful as a colorant (typically yellow, orange and especially red in color) but also provides a valuable source of vitamin A. Most of the other carotenoids have also further beneficial properties in addition to their coloring capacity. For this reason, carotenoids are often included in foods and beverages as a colorant, especially where their further beneficial property, such as vitamin A fortification, is needed or desired.

Carotenoids have per se a very limited solubility in water. Thus, they have to be transformed into forms which are water-soluble if they are supposed to be incorporated into beverages. This is usually done by embedding the carotenoids in a matrix of hydrocolloids such as gelatin and starch. These water-soluble, usually powdery forms have to fulfil certain criteria. They e.g. have to be stable and not to set free the carotenoids in the final composition, such as a beverage or a food composition, prior to consumption. Concerning the use in beverages it is also desired that the forms completely dissolve in the beverage and do not form a ring on the surface of the container (so-called "ringing") wherein the beverage is either stored or provided for consumption.

It was therefore an object of the following invention to provide a dispersion containing one or more carotenoids, in a preferred embodiment a powder containing one or more carotenoids (in the following also collectively referred to as "forms") wherein especially the powder should be suitable in beverages.

Furthermore it was an object of the invention to provide a process for the manufacture of said forms that would be feasible or useful in industrial scale.

It has surprisingly been found that the object of the present invention is achieved by a process for the manufacture of an emulsion or dispersion containing one or more carotenoids comprising the steps of
 a) dispersing one or more carotenoid(s) and one or more triglyceride(s) in a solvent;
 b) dissolving a hydrocolloid in water, wherein the concentration of the hydrocolloid in the so-derived aqueous matrix solution is in the range of from 20 to 50 weight-%, based on the total weight of the matrix solution;
 c) mixing the dispersion of step a) with the matrix solution of step b);
 d) homogenizing the thus resulting mixture of step c);
 e) removing the solvent;
 f) filtrating the mixture with a multi-layer filter to separate a precipitated insoluble fraction of particles having an average particle size in the range of from 1 to 500 µm.

Step e) and f) of the process according to the present invention can be conducted at any order. It is preferable to carry out step e) prior to step f).

According to the present invention the carotenoid is preferably chosen from astaxanthin, canthaxanthin, lycopene, lutein, zeaxanthin, crocetin, α-zeacarotene, β-zeacarotene, α-carotene, β-carotene, 8'-apo-β-carotenal, 8'-apo-β-carotenoic acid esters, or mixtures thereof. Preferred are canthaxanthin, lycopene, β-carotene, 8'-apo-β-carotenal; β-carotene is especially preferred.

Figure 1:
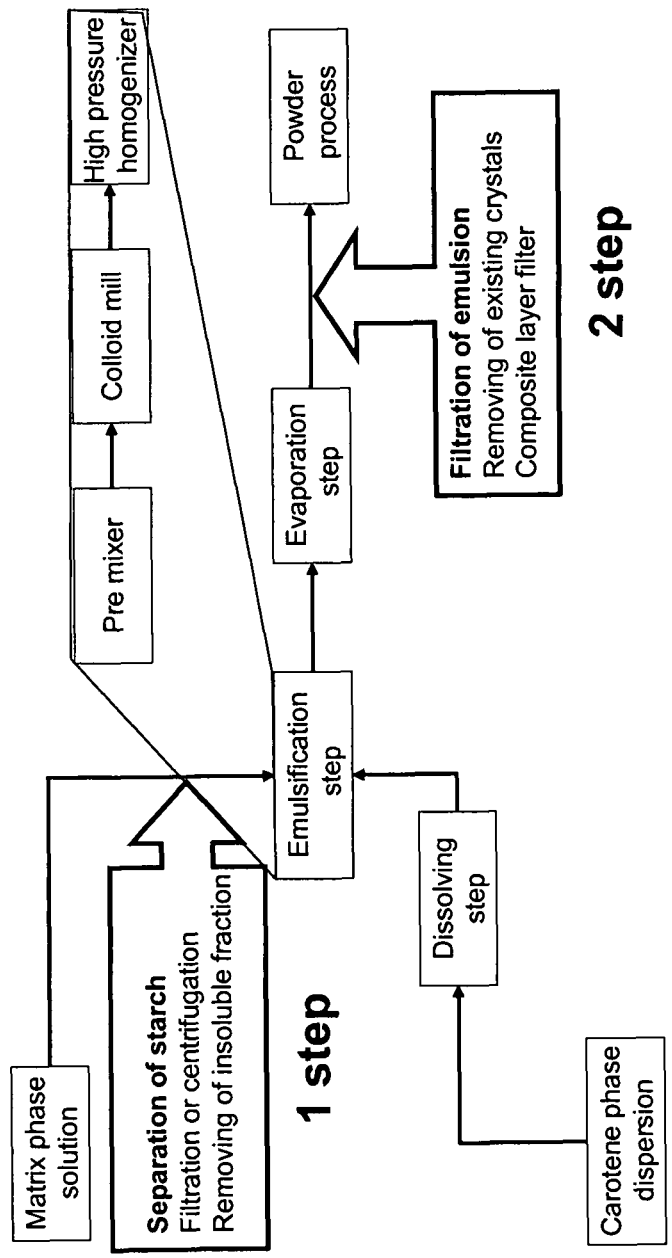
FIG. 1 shows a scheme of the formulation process according to the present invention.

The single steps are now disclosed in more detail in the following.

Step a)

The carotenoid (one or more compounds) is just mixed with the solvent and dispersed.

The triglyceride used in step a) is preferably selected from vegetable oils and/or fats, preferably corn oil, sunflower oil, (hydrogenated) soybean oil, safflower oil, rape seed oil, peanut oil, (hydrogenated) palm oil, palm kernel oil, cotton seed oil and/or coconut oil, including fractionated qualities thereof. The triglycerides can preferably be so-called MCT (medium chain triglycerides), i.e. ester of medium chain fatty acids (preferably saturated fatty acids with a chain length of 6 to 12 C atoms) and glycerol. Preferred triglycerides are corn oil, sunflower oil, (hydrogenated) soybean oil and/or (hydrogenated) palm oil.

The solvent used in step a) may be water or a water-miscible or water-immiscible organic solvent, while water-immiscible organic solvents are preferred.

According to the present invention the term "water-miscible organic solvent" denotes an organic solvent having a solubility in water of more than or equal to 10% under atmospheric pressure, such as water-miscible alcohols, ethers, esters, ketons and/or acetals. Preferred water-miscible organic solvents are ethanol, n-propanol, iso-propanol, 1,2-butanediol-1-methylether, 1,2-propanedioil-1-n-propylether, acetone or mixtures thereof.

According to the present invention the term "water-immiscible organic solvent" denotes an organic solvent having a solubility in water of less than 10% under atmospheric pressure. Preferred water-immiscible organic solvents are halogenated aliphatic hydrocarbons, such as e.g. chloroform, carbon tetra-chloride and methylene chloride, water-inmiscible esters, such as e.g. carbonic acid dimethylester (dimethyl carbonate), formic acid ethylester (ethyl formate), methyl-, ethyl-, or isopropylacetate; or water-inmiscible ethers, such as e.g. methyl-tert. butylether and the like. Preferred are dimethyl carbonat, ethyl formate, ethyl- or isopropylacetate, methyl-tert. butylether or mixtures thereof.

Step b)

Step b) of the process according to the present invention can be conducted at any reasonable temperature to ensure a rapid dissolution of the hydrocolloid in water. To maximize dissolution of the hydrocolloid within a reasonable amount of time, heating to about 40 to 80° C. is preferable.

The aqueous matrix solution is obtained by adding the hydrocolloid to water (usually under stirring) until its concentration is in the range of from 20 to 50 weight-%, based on the total weight of the matrix solution.

The term "hydrocolloid" as used herein includes gelatine, xanthan gum, acacia gum, pectins, guar, caroub gums, alginates, celluloses, cellulose derivatives, such as carboxymethylcellulose, and/or modified polysaccharides.

The term "modified polysaccharide" as used herein relates to polysaccharides which contain a lipophilic moiety, e.g. a hydrocarbon moiety having a chain length of preferably 5 to 18 carbon atoms in the straight chain. Preferably the modified polysaccharide should be acceptable for human consumption, i.e. preferred modified polysaccharides should be GRAS (generally recognized as safe) or approved for food consumption as determined by the various regulatory agencies world wide. A preferred modified polysaccharide is modified food starch.

The term "modified food starch" as used herein relates to modified starches that are made from starches substituted by known chemical methods with hydrophobic moieties. For example starch may be treated with cyclic dicarboxylic acid anhydrides such as succinic and/or glutaric anhydrides, substituted with an alkyl or alkenyl hydrocarbon group.

A particularly preferred modified starch of this invention has the following formula (I)

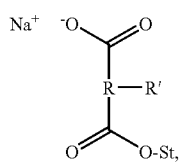

(I)

wherein St is a starch, R is an alkylene radical and R' is a hydrophobic group. Preferably R is a lower alkylene radical such as dimethylene or trimethylene. R' may be an alkyl or alkenyl group, preferably having 5 to 18 carbon atoms. A preferred modified starch of formula (I) is starch sodium octenyl succinate ("OSA-starch"). The term "OSA-starch" as used herein denotes any starch (from any natural source such as corn, wheat, tapioca, potatoe or synthesized) that was treated with octenyl succinic anhydride (OSA). The degree of substitution, i.e. the number of esterified hydroxyl groups with regard to the total number of hydroxyl groups usually varies in a range of from 0.1° A) to 10%, preferably in a range of from 0.5% to 5° A), more preferably in a range of from 2% to 4%.

OSA-starches may contain further hydrocolloids, such as starch, maltodextrin, carbohydrates, gum, corn syrup etc. and optionally any typical emulsifier (as co-emulgator), such as mono- and diglycerides of fatty acids, polyglycerol esters of fatty acids, lecithins, sorbitan monostearate, and plant fibre or sugar.

OSA-starches are commercially available e.g. from National Starch under the trade names HiCap 100, Capsul, Capsul HS, Purity Gum 2000, UNI-PURE, NYLON VII; from Roquette Freres; from CereStar under the tradename C*EmCap or from Tate & Lyle.

The terms "modified polysaccharides", "modified starches" and "OSA-starches" encompass further also modified polysaccharides/modified starches/OSA-starches that were partly hydrolysed enzymatically, e.g. by glycosylases (EC 3.2; see http://www.chem.qmul.ac.uk/iubmb/enzyme/EC3.2/), as well as to modified poly-accharides/modified starches/OSA-starches that were partly hydrolysed chemically by know methods.

The enzymatical hydrolysis is conventionally carried out at a temperature of from about 5 to about <100° C., preferably at a temperature of from about 5 to about 70° C., more preferably at a temperature of from about 20 to about 55° C.

The glycosylases can be from fruit, animal origin, bacteria or fungi. The glycolase may have endo-activity and/or exo-activity. Therefore, enzyme preparations of endo- and exo glycosylases or any of their mixtures may be used. Preferably the glycosylases have pectolytic and/or hemicelluloytic activity. Usually the glycosylases show also unknown side activities, but which are not critical for the manufacture of the desired product.

Examples of glycosylases are the commercially available enzyme preparations from the suppliers Novozymes, Genencor, AB-Enzymes, DSM Food Specialities, Amano, etc.

The glycosylase is added to provide a concentration of from about 0.01 to about 10 weight-%, preferably of from about 0.1 to about 1 weight-%, based on the dry weight of the modified polysaccharide/modified starch/OSA-starch. In a preferred embodiment of the process of the invention, the enzyme is added at once. The enzymatic hydrolysis may also be carried out stepwise. For instance, the glycosylase or a mixture of glycosylases is added to the incubation batch in an amount of e.g. 1% whereupon, e.g. after 5 to 10 minutes (at a temperature of 35° C.) further glycosylase or a mixture of glycosylases which may by the same or different from the first added glycosylase or mixture of glycosylases is added, e.g. in an amount of 2% whereupon the incubation batch is hydrolysed at 35° C. for 10 minutes. Using this procedure, starting modified polysaccharides/modified starches/OSA-starches having a degree of hydrolysis of approximately zero can be used.

The duration of hydrolysis may vary between about a few seconds and about 300 minutes. The exact duration of the enzymatic treatment may be determined in an empirical way with respect to the desired properties of the modified polysaccharide/modified starch/OSA-starch, such as emulsifying stability, emulsifying capacity, droplet size of the emulsion, depending strongly on parameters like enzyme activities, or composition of the substrate. Alternatively it may be determined by measuring the osmolality (W. Dzwokak and S. Ziajka, Journal of food science, 1999, 64 (3)393-395).

The inactivation of the glycosylase is suitably achieved by heat denaturation, e.g. by heating of the incubation batch to about 80 to 85° C. for 5 to 30 minutes, especially for 5 to 10 minutes.

In an especially preferred embodiment of the present invention the carotenoid is beta-carotene and the hydrocolloid is a modified polysaccharide, most preferred modified food starch.

If the hydrocolloid dissolved in water in step b) is a modified polysaccharide it may be advantageous to separate a possible solid insoluble fraction from the matrix solution obtained in step b) in an intermediate step b1) before mixing the dispersion of step a) with the matrix solution of step b).

By "solid insoluble fraction" in the context of the present invention preferably a fraction is meant which is not soluble at atmospheric pressure in water of a temperature in the range of from 1 to <100° C., more preferably a fraction which is not soluble in water of a temperature in the range of from 30 to <100° C., most preferably a fraction which is not soluble in water of a temperature in the range of from about 40 to 80° C.

The solid insoluble fraction may be separated from the matrix solution obtained in step b) by centrifugation or by filtration, preferably by microfiltration, especially preferred by crossflow microfiltration or by both.

Centrifugation is a method which separates according to the density, filtration is a method that separates according to the particle size.

The centrifugation may be carried out at 1'000 to 20'000 g depending on the dry mass content of the modified polysaccharide in the aqueous solution or suspension. If the dry mass content of the modified polysaccharide in the aqueous solution or suspension is high, the applied centrifugation force is also high. For example for an aqueous solution or suspension with a dry mass content of the modified polysaccharide of 30 weight-% a centrifugation force of 12'000 g may be suitable to achieve the desired separation.

By "microfiltration" in the context of the present invention is meant that particles that have an average size in the range of from 400 nm to 500 μm, preferably from 500 nm to 100 μm, more preferably from 1 μm to 50 μm are separated.

The aqueous matrix solution of step b) may be prepared with warm water (water of a temperature of from >30 to <100° C.) (step b)) and may be filtered or sedimentated also at this temperature (step b1)), or it may then be cooled down to a temperature of below 30° C., and filtered or sedimentated at this lower temperature (step b1)).

In a preferred embodiment of the present invention the aqueous matrix solution of step b) is prepared with cold water (water of a temperature of from 1 to 30° C.) (step b)) and is also filtered or sedimentated at this temperature (step b1)).

In a further preferred embodiment of the present invention additionally the pH of the aqueous solution of the modified polysaccharide is adjusted to a value of from 2 to 5.

In a technical process steps a) and b) (and optionally b1)) are usually performed at the same time/parallel in different vessels.

In a preferred embodiment of the process of the present invention further adjuvants may be added to the dispersion. The further adjuvants may be added if water-soluble during step b) or if fat-soluble during step a) and are preferably selected from one or more of the following groups:
 diluents;
 antioxidants (fat-soluble or water-soluble);
Preferred diluents can be selected from glycerol, mono-, di- and oligosaccharides. According to the present invention sucrose, invert sugar, glucose, fructose, lactose, maltose, saccharose, sugar alcohols and starch hydrolysates, such as dextrins, maltodextrins and/or glucose syrup.

According to the present invention it is advantageous if the amount of diluents (one or more compounds) in the mixture of step c) is in the range of from 1 to 20% by weight, preferably from 10 to 15% by weight, each based on the total weight of the mixture.

Preferred water-soluble antioxidants are for example ascorbic acid or salts thereof, preferably sodium ascorbate. Preferred fat-soluble antioxidants are for example tocopherol (synthetic or natural); butylated hydroxytoluene (BHT); butylated hydroxyanisole (BHA); propyl gallate; tert. butyl hydroxyquinoline and/or ascorbic acid esters of a fatty acid, preferably ascorbyl palmitat and/or ascorbyl stearate. dl-Tocopherol is especially preferred.

Step c)

Step c) is performed by adding the solution resulting in step b) (and optionally b1)) to the dispersion obtained in step a) or vice versa.

Step d)

The homogenization is performed by passing the mixture obtained in step c) preferably several times) through a high pressure homogenizer or by ultrasonification or any other method known by the person skilled in the art.

Step e)

The solvent is removed using conventional methods e.g. by evaporation.

Step f)

Preferably the particles to be separated have an average particle size in the range of from 1 to 200 μm.

The emulsion or dispersion obtained in step d) as disclosed above is filtrated through a multi-layer filter with a capacity in the range of from 400 to 1000 kg/m². The flow direction through the multi-layer filter is different to a normally used filter with graded-density layers. The principle of multi-layer filter according to the present invention is to pass the filter from low to high density layers. The particles to be separated will accordingly be absorbed in the depth of the filter material. The first layer removes the largest particles, the last layer the smallest particles.

The multi-layer filters according to the present invention are filters with graded-density layers and disposable filter bags. They are e.g. commercially available from LIGACON W.Röll & CO. AG (Switzerland). For the purpose of the present invention they have at least 5 active layers, preferably up to 10 layers, with different cut ranges; preferred cut ranges are in the range of from 0.5 to 25 μm, more preferred range of from 1 to 5 μm. Preferably at least 3 layers are made out of the layer with the smallest size.

In a preferred embodiment of the present invention the multi-layer filter is an ULTRAFIT® 500 filter bag (commercially available from Filtration Systems, Florida, USA) consisting of 5 graded-density layers of melt-blown polypropylene microfiber layers with a preferred cut range from 0.5 to 25 μm, more preferred from 1 to 5 μm. In a preferred embodiment the filter further contains two layers of ultrasonically laminated polypropylene monofilament and two layers of non-woven spun bond.

In the emulsion or dispersion obtained in step f) the carotenoid particles have an average particle size in the range of from 100 to 700 nm, preferably in the range of from 200 to 500 nm, more preferably in the range of from 200 to 350 nm.

The present invention does not only encompass the processes as disclosed above, but any other process for the manufacture of emulsions or dispersions containing carotenoids (with the preferences as mentioned above) known to the person skilled in the art wherein step f) according to the present invention is performed.

Thus, the present invention is also directed to a process for the filtration of emulsions or dispersions containing carotenoids having two different sized fractions or a corresponding particle size-distribution of the carotenoid particles, wherein the fraction to be separated has particles with an average particle size in the range of from 0.7 to 500 µm, and wherein the fraction to be obtained has particles with an average particle size in the range of from 100 to 700 nm, comprising the step of separating the fraction with the particles having a size in the range of from 0.7 to 500 µm by filtration with a multi-layer filter by letting the emulsion or dispersion pass the filter from low to high density layers.

The processes according to the present invention may preferably be used if the amount of the fraction to be separated is below 1 weight-%, based on the total weight of said emulsion or dispersion.

Furthermore, the present invention is also directed to the use of a multi-layer filter as defined above for the filtration of emulsions/dispersions containing carotenoids (with the preferences as disclosed above), preferably containing carotenoids selected from the group consisting of canthaxanthin, lycopene, β-carotene, 8'-apo-β-carotenal and any mixture thereof, more preferably containing β-carotene.

The present invention is also directed to the emulsion or dispersion obtained by the process of the present invention as disclosed above. Furthermore the present invention is further directed to emulsions or dispersions having the same properties but obtained by different processes, i.e. emulsions or dispersions obtainable according to the process of the present invention.

Emulsions or dispersion obtained/obtainable according to the process of the present invention comprise one or more carotenoid(s), one or more hydrocolloid(s), water, optionally one or more antioxidant/s, and optionally one or more triglyceride(s), wherein the average particle size of said carotenoid(s) is in the range of from 100 to 700 nm.

Preferably the emulsion or dispersion according to the present invention comprises from 0.5 to 10 weight-% of said carotenoid(s), from 20 to 35 weight-% of said hydrocolloid(s), from 55 to 75 weight-% of water, optionally from 0.1 to 1 weight-% of antioxidant(s), and optionally from 0.2 to 3 weight-% of triglyceride(s), each based on the total weight of said emulsion or dispersion.

In an especially preferred embodiment of the present invention the emulsions or dispersion obtained/obtainable according to the process of the present invention comprise beta-carotene as carotenoid and a modified polysaccharide, most preferred modified food starch as hydrocolloid.

A preferred emulsion or dispersion composition is given in the following table:

| Composition | wt % |
| --- | --- |
| active ingredient (beta Carotene) | 5.50 |
| alpha Tocopherol | 0.66 |
| oil (hydrated soybean-oil) | 1.98 |
| Modified starch (HiCap 100) | 23 to 29 |
| Water | add 100 |

It has now been found that emulsions or dispersions manufactured according to the process of the present invention show superior performance especially with respect to their use in beverages in comparison to forms manufactured according to a process without a filtration step f).

The emulsion or dispersion obtained/obtainable by the process of the present invention is an oil-in-water dispersion and can especially preferred be converted after removal of the solvent (if still present) into a solid composition (in the following also referred to as "solid form"), e.g. a dry powder, by performing an additional drying step g).

Step g)

The drying step may be carried out with any conventional drying process known to the person skilled in the art, preferred are freeze-drying, spray drying, spray drying in combination with fluidised bed granulation (commonly known as fluidised spray drying or FSD) and/or a powder catch process (resulting in so-called beadlets) where sprayed emulsion or dispersion droplets are caught in a bed of an absorbant such as starch or calcium silicate or silicic acid or calcium carbonate or mixtures thereof and subsequently dried.

According to the present invention it is advantageous if the residual moisture content in the powder obtained by the drying step g) is in the range of from 0.5 to 7.0 weight-%, preferably from 4 to 6 weight-%, each based on the total weight of the powder.

The freeze-drying is preferably performed at a temperature of from −20° C. to −50° C. for 10 to 48 hours.

In a preferred embodiment the emulsion or dispersion obtained/obtainable by the process of the present invention is spray-dried. In this case it is preferred to select the spray drying parameters as follows:

Air inlet: from about 100° C. to about 250° C., preferably of from 150° C. to about 200° C., more preferably of from about 160° C. to about 190° C.;

Air exit: from about 45° C. to about 160° C., preferably of from about 55° C. to about 110° C., more preferably of from about 65° C. to about 95° C.

The solid form may be further dried and/or granulated.

The present invention is also directed to the solid forms (dry powders, beadlets or granul(at)es) obtained by the process of the present invention as disclosed above.

Furthermore the present invention is further directed to solid forms having the same properties but obtained by different processes, i.e. solid forms obtainable according to the process of the present invention.

The solid form of carotenoids obtained/obtainable according to the present invention comprises one or more carotenoid(s), one or more hydrocolloid(s), water, optionally one or more antioxidant/s, and optionally one or more triglyceride(s).

Preferably the solid form according to the present invention comprises from 1 to 20 weight-% of carotenoid(s), from 40 to 75 weight-% of hydrocolloid(s), from 0.5 to 7.0 weight-% of water, optionally from 0.5 to 3 weight-% of antioxidant(s), and optionally from 1 to 10 weight-% of triglyceride(s), each based on the total weight of said solid form.

In an especially preferred embodiment of the present invention solid form according to the present invention comprises beta-carotene as carotenoid and a modified polysaccharide, most preferred modified food starch as hydrocolloid.

A preferred composition of a solid form is given in the following table:

| Composition | wt % |
| --- | --- |
| active ingredient (beta Carotene) | 12.50 |
| alpha Tocopherol | 1.50 |
| oil (hydrated soybean-oil) | 5.50 |
| Modified starch (HiCap 100) | 53.24 |
| corn starch | 22.00 |
| Water | 5.00 |

The present invention is also directed to the use of the solid form according to the present invention for the enrichment, fortification and/or coloration of food, beverages, animal feed, dermatological or pharmaceutical preparations.

The solid forms obtained/obtainable by the process of the present invention show excellent performance in beverages, in particular no surface layer is build at the bottle neck in beverages.

Other aspects of the invention are beverages, food, animal feed, dermatological and pharmaceutical preparations, especially beverages, containing a solid form and/or an emulsion or dispersion according to the present invention.

Beverages wherein the solid form of the present invention can be used as a functional ingredient can be carbonated beverages e.g., flavoured seltzer waters, soft drinks or mineral drinks, as well as non-carbonated beverages e.g. flavoured waters, fruit juices, fruit punches and concentrated forms of these beverages. They may be based on natural fruit or vegetable juices or on artificial flavours. Also included are alcoholic beverages and instant beverage powders. Besides, sugar containing beverages diet beverages with non-caloric and artificial sweeteners are also included.

Further, dairy products, obtained from natural sources or synthetic, are within the scope of the food products wherein the solid forms of the present invention can be used as a functional ingredient. Typical examples of such products are milk drinks, ice cream, cheese, yoghurt and the like. Milk replacing products such as soymilk drinks and tofu products are also comprised within this range of application.

Also included are sweets which contain the solid form of the present invention as a functional ingredient, such as confectionery products, candies, gums, desserts, e.g. ice cream, jellies, puddings, instant pudding powders and the like.

Also included are cereals, snacks, cookies, pasta, soups and sauces, mayonnaise, salad dressings and the like which contain the solid form of the present invention as a functional ingredient. Furthermore, fruit preparations used for dairy and cereals are also included.

The final concentration of the carotenoid which is added via the solid form of the present invention to the food products may be from 0.1 to 500 ppm, particularly from 1 to 50 ppm based on the total weight of the food composition and depending on the particular food product to be coloured or fortified and the intended grade of coloration or fortification.

The food compositions of this invention are preferably obtained by adding to a food product the carotenoid in a solid form according to the present invention. For coloration or fortification of a food or a pharmaceutical product a solid form of this invention can be used according to methods per se known for the application of water dispersible solid product forms.

In general the carotenoid composition may be added either as an aqueous stock solution, a dry powder mix or a pre-blend with other suitable food ingredients according to the specific application. Mixing can be done e.g. using a dry powder blender, a low shear mixer, a high-pressure homogeniser or a high shear mixer depending on the formulation of the final application. As will be readily apparent such technicalities are within the skill of the expert.

Pharmaceutical preparations such as tablets or capsules wherein the solid form is used as a colorant are also within the scope of the present invention. The coloration of tablets can be accomplished by adding the solid form in form of a solid colorant composition or—after dissolving in a solvent, preferably water—as liquid composition separately to the tablet coating mixture or by adding a colorant composition to one of the components of the tablet coating mixture. Coloured hard or soft-shell capsules can be prepared by incorporating a colorant composition in the aqueous solution of the capsule mass.

Pharmaceutical preparations such as tablets, e.g. chewable tablets, effervescent tablets or filmcoated tablets, or capsules such as hard shell capsules wherein the solid form is used as an active ingredient are also within the scope of the present invention. The solid forms is typically added as powder to the tableting mixture or filled into the capsules in a manner per se known for the production of capsules.

Animal feed products such as premixes of nutritional ingredients, compound feeds, milk replacers, liquid diets or feed preparations wherein the solid form is either used as a colorant for pigmentation e.g. for egg yolks, table poultry, broilers or aquatic animals or as an active ingredient are also within the scope of the present invention.

Cosmetics, toiletries and derma products i.e. skin and hair care products such as creams, lotions, baths, lipsticks, shampoos, conditioners, sprays or gels wherein the solid form is used as a colorant or as an active ingredient are also within the scope of the present invention.

The following non limiting examples illustrate the invention further.

EXAMPLES

Comparative Example 1

Filtration with a Porous Steel Filter

An emulsion containing 8 weight-% of β-carotene was filtered through a porous steel pipe-filter, commercially available from LIGACON W.Röll & CO. AG (Switzerland), wherein the size of the pores was 5 μm. The achieved capacity was about 7 kg/m² before the filter was completely blocked although a crossflow filtration was used. This capacity is too low to lead to an industrial economic process.

Comparative Example 2

Filtration with Multi-Layer Mesh Filters

An emulsion containing 8 weight-% of β-carotene was filtered through a sintered mesh filters commercially available from G.BOPP AG (Switzerland). The sintered mesh consists of five graded-density layers of sintered metal meshes. The permeate passes the filter from mesh with small mesh size to the layers with large mesh size. By a graded-density layer filter on the first layer with the smallest mesh size is relevant for the filtration cut. The function of the other meshes is to guarantee the needed resistance of the filtration surface against the pressure drop over the filter. Tested mesh size were 2, 5, 10 μm (layer with the smallest mesh size).

The mesh filters blinded more or less immediately by the insoluble fraction of the starch. The achieved capacity was only 9 kg/m². Also crossflow filtration could not increase the capacity.

Example 1

Formulation Process According to the Present Invention Including Filtration with a Composite Layer Filter FIG. 1 shows a scheme of the formulation process according to the present invention. The formulation process contained two separation steps: the first separation step was the filtration or centrifugation of the starch solution (the "matrix"), the second separation step was the filtration of the emulsion.

The matrix phase was an aqueous solution of HiCap 100, commercially available from National Starch, Mangester, USA, containing chemically modified food starch refined from waxy maize (EU classification: E1450). The concentration of HiCap®100 varied between 10 to 50 wt-%, based on the total weight of the matrix solution.

90 g of β-carotene were dissolved in methylene chloride at a temperature in the range of from 60 to 75° C. and at about 7 bar pressure resulting in an 8 weight-% solution of β-carotene in methylene chloride. To this solution 39 g of an oil (hydrogenated soybean oil, hydrogenated palm oil or corn oil) were added. This solution was stirred for 30 minutes In a separate vessel 338 g of centrifuged, spray dried HiCap®100 were dissolved/dispersed in water at 50° C. and at atmospheric pressure resulting in a 29 weight-% solution/dispersion of that starch in water.

The lipophilic phase containing β-carotene, methylene chloride and the oil and the hydrophilic phase containing water and HiCap®100 were mixed together. The resulting emulsion was homogenized in the first step using rotor stator device (speed 5000 rpm) at a temperature of 66° C. In the second step the pre-emulsion is further homogenised by passing over a nozzle (diameter 200 μm) with a pressure drop of 118 bar at 65° C. Then the methylene chloride was evaporated by a cascade of two thin film evaporators at 31° C. and 429 mbar in the first evaporator and 60° C. at 498 mbar for the second evaporator. The resulting concentrated emulsion was then filtered.

The filtration trials were done by a lab-filtration tool with 0.00159 m² filter discs. The attached figures show the achieved flow over the time for a filtration surface of 1 m². The capacity depends on which flow down the filter will be used. So, by increasing the filtration surface the capacity per m² could be increased because the filters could be used at a lower flow rate.

The figures show also the pressure drop over the filters.

The ULTRAFIT® 500 filter bag consists of 5 graded-density layers of melt-blown polypropylene microfiber layers, [preferred cut range from 1 to 25 μm, more preferred range 1 to 5 μm] and further 2 layers of ultrasonically laminated polypropylene monofilament and 2 layers of non-woven spun bond. Supplier for such filters is LIGACON W.Röll & CO. AG (Switzerland)

Comparative Example 3

Formulation Process without Separation of the Insolubles Parts from the Starch An emulsion was prepared as described in example 1 by using instead of separated starch not purified HiCap®100 from national starch. The so produced emulsion was filtered through the 10 μm multi-layer filter ULTRAFIT® 500-P010, commercially available from LIGACON W. Röll & CO. AG (Switzerland). The used filter blinded more or less immediately by the insoluble fraction of the starch. The achieved capacity was only 36 kg/m².

Example 2

(Embodiment of the Present Invention): Forms with Hydrogenated Soybean Oil

The emulsion was prepared as described in example 1 by using hydrogenated soybean oil as adjuvant for dissolving β-carotene. The hydrogenated soybean oil was purchased from ADM (Decatur Ill., USA); it had a melting point in the range of from 66 to 68° C. and a saturation grade of 95%. The emulsion was then either filtered according to alternative a) or according to alternative b).

a) The emulsion was filtered through the 2 μm multi-layer filter ULTRAFIT® 500-P002, commercially available from LIGACON W. R$_{oll}$ & CO. AG (Switzerland). The achieved capacity was 600 kg/m² (see FIG. 2).

Figure 2:
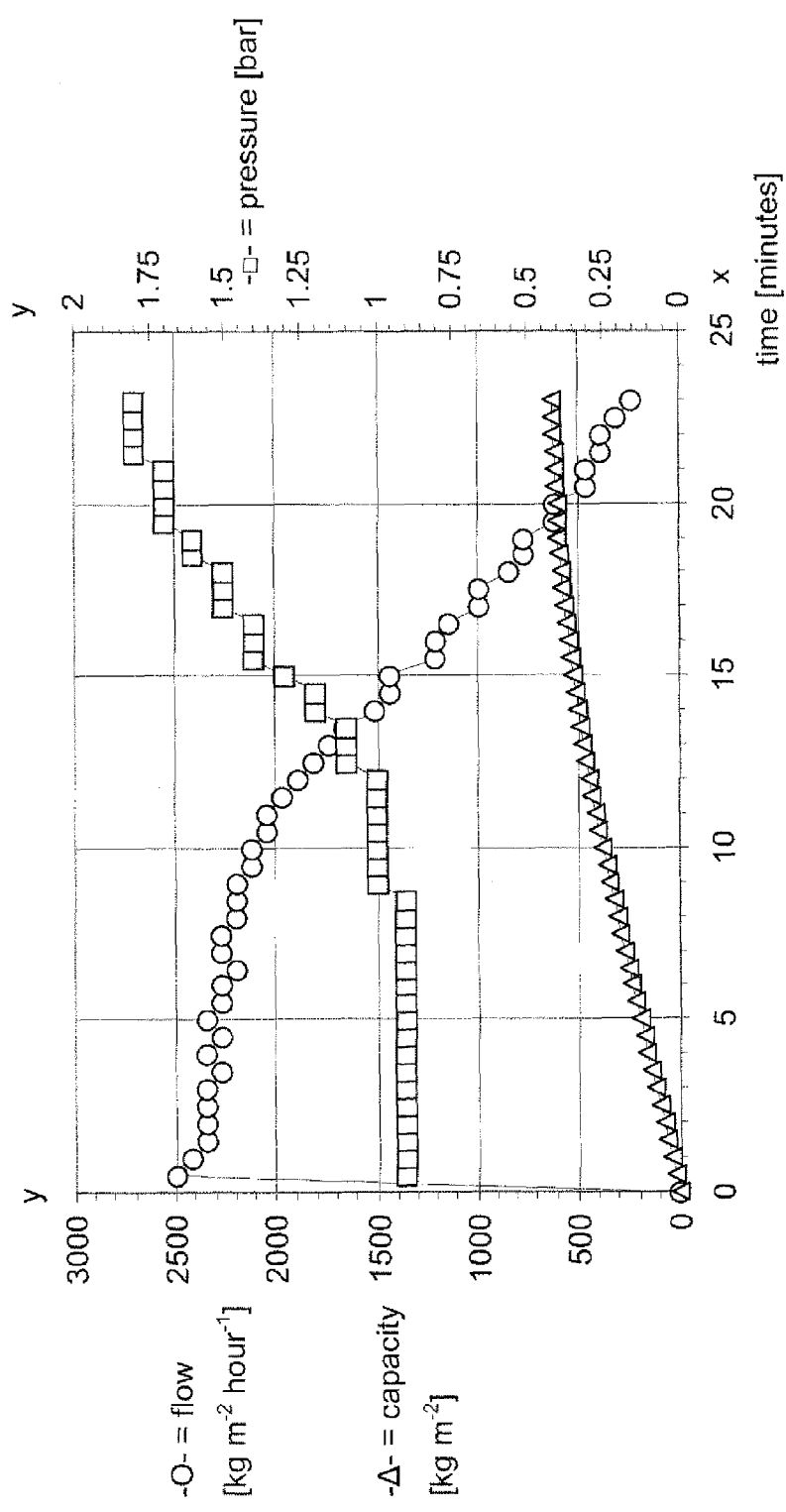
FIG. 2 shows the flow and capacity for the filtration step of hydrogenated soybean oil with a 2 µm multilayer filter (Typ Ultrafit 500-P002).

FIG. 2 shows the flow and capacity for the filtration step of hydrogenated soybean oil with a 2 μm multilayer filter (Typ Ultrafit 500-P002). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

b) The emulsion was filtered through the 5 μm multi-layer filter ULTRAFIT® 500-P005, commercially available from LIGACON W. Röll & CO. AG (Switzerland). The achieved capacity was 1000 kg/m² (see FIG. 3).

Figure 3:
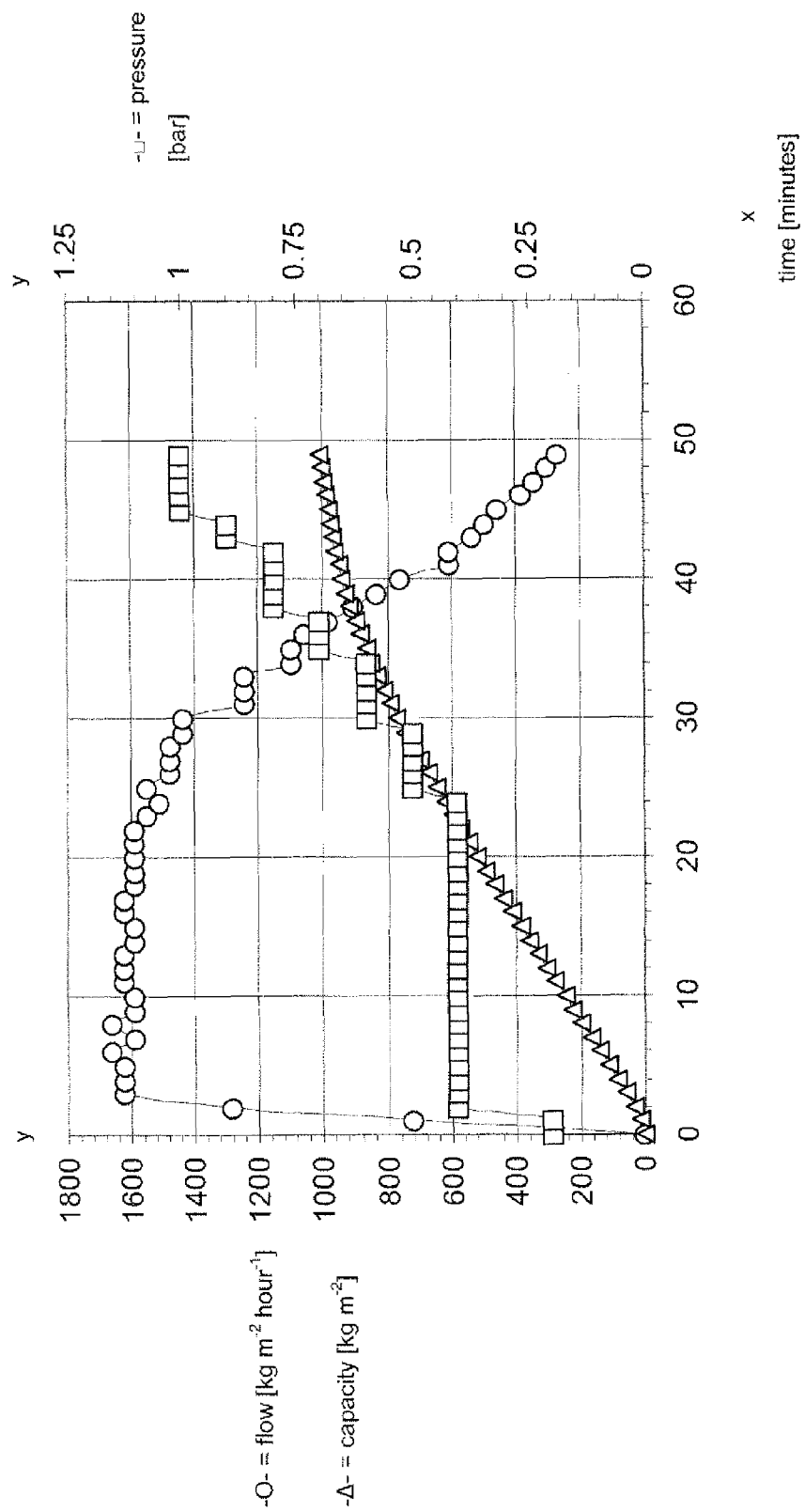
FIG. 3 shows the flow and capacity for the filtration step of hydrogenated soybean oil with a 5 gm multilayer filter (Typ Ultrafit 500-P005).

FIG. 3 shows the flow and capacity for the filtration step of hydrogenated soybean oil with a 5 μm multilayer filter (Typ Ultrafit 500-P005). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

The filtration trials a) and b) for the emulsion containing hydrogenated soybean oil show both a good filtration capacity.

Example 3

(Embodiment of the Present Invention): Forms with Hydrogenated Palm Oil

The emulsion was prepared as described in example 1 by using hydrogenated palm oil as adjuvant for dissolving β-carotene. The hydrogenated palm oil was purchased from Florin (Switzerland); it has a melting point in the range of from 45 to 48° C., and a saturation grade of 49%. The emulsion was then either filtered according to alternative a) or according to alternative b) or according to alternative c).

a) The emulsion was filtered through the 2 μm multi-layer filter ULTRAFIT® 500-P002, commercially available from LIGACON W. Röll & CO. AG (Switzerland). The achieved capacity was 80 kg/m² (see FIG. 4).

Figure 4:
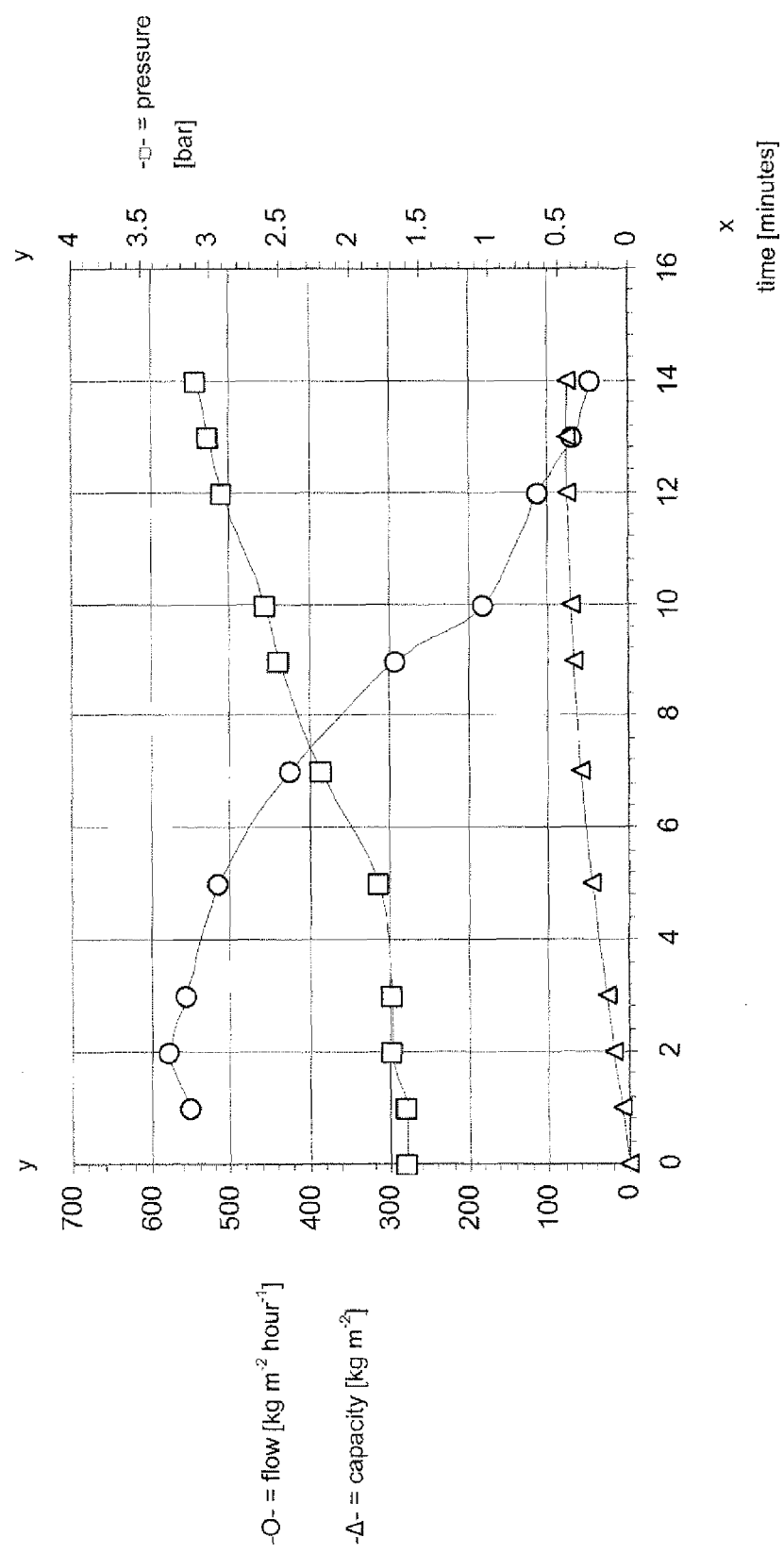
FIG. 4 shows the flow and capacity for the filtration step of hydrogenated palm oil with a 2 µm multilayer filter (Typ Ultrafit 500-P002).

FIG. 4 shows the flow and capacity for the filtration step of hydrogenated palm oil with a 2 μm multilayer filter (Typ Ultrafit 500-P002). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

b) The emulsion was filtered through the 10 μm multi-layer filter ULTRAFIT® 500-P010, commercially available from LIGACON W. Röll & CO. AG (Switzerland). The achieved capacity was about 100 kg/m² (see FIG. 5).

Figure 5:
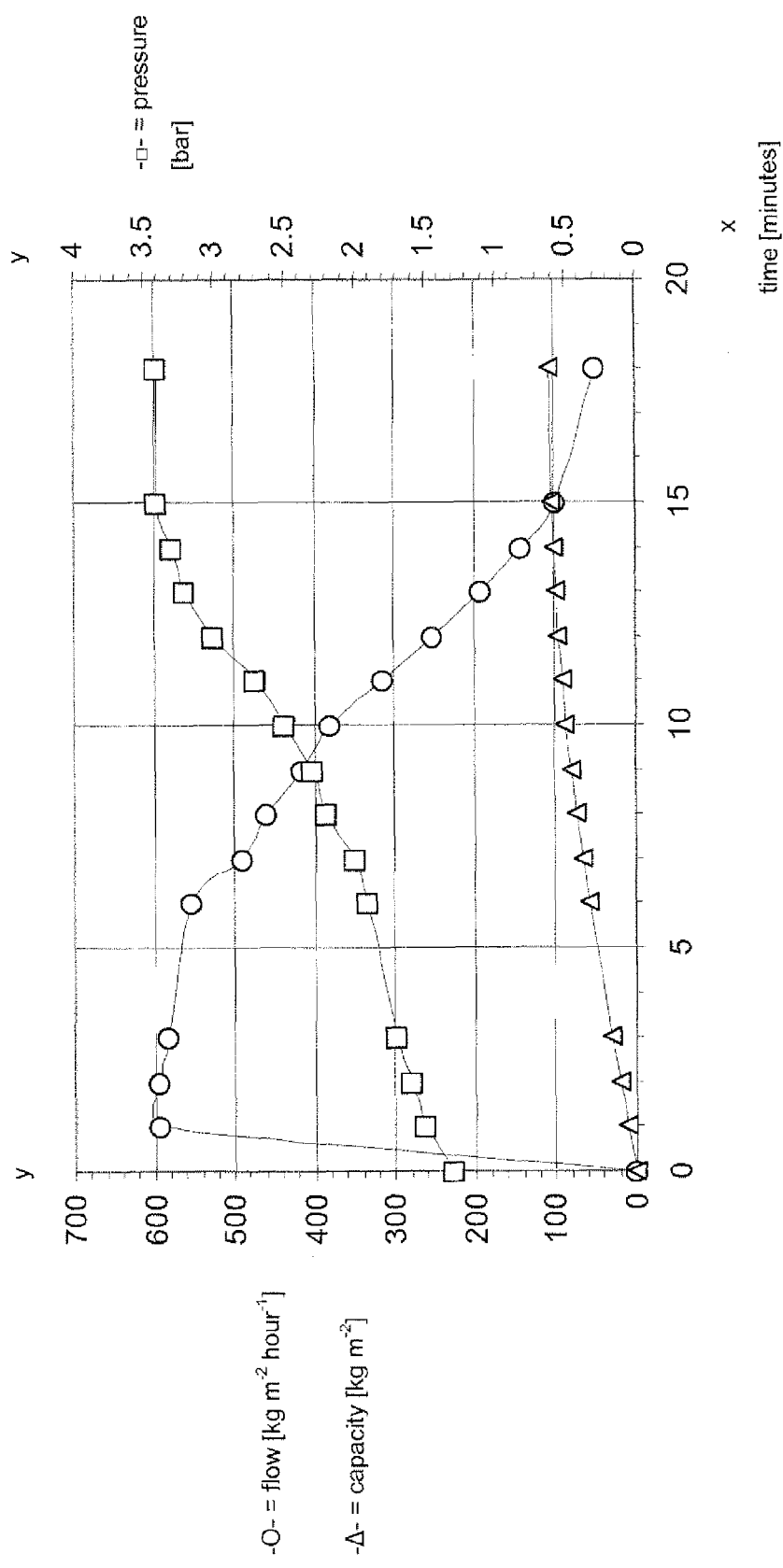
FIG. 5 shows the flow and capacity for the filtration step of hydrogenated palm oil with a 10 µm multilayer filter (Typ Ultrafit 500-P010).

FIG. 5 shows the flow and capacity for the filtration step of hydrogenated palm oil with a 10 μm multilayer filter (Typ Ultrafit 500-P010). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

c) The emulsion was filtered through the 25 μm multi-layer filter ULTRAFIT® 500-P025, commercially available from LIGACON W.Röll & CO. AG (Switzerland). The achieved capacity was 120 kg/m² (see FIG. 6).

Figure 6:
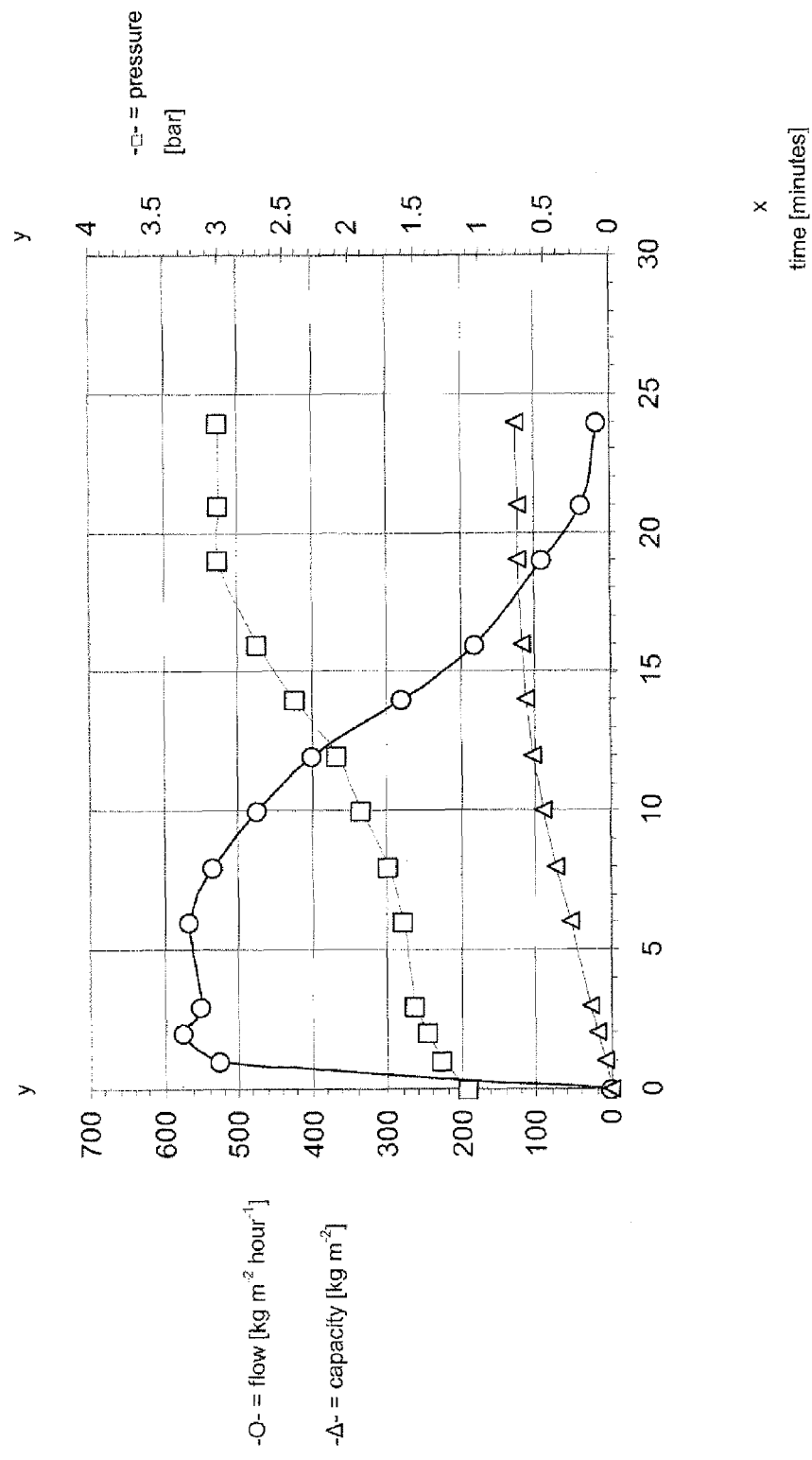
FIG. 6 shows the flow and capacity for the filtration step of hydrogenated palm oil with a 25 µm multilayer filter (Typ ULTRAFIT® 500-P025).

FIG. 6 shows the flow and capacity for the filtration step of hydrogenated palm oil with a 25 μm multilayer filter (Typ ULTRAFIT® 500-P025). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

The filtration trials a) to c) with the hydrogenated palm oil show much lower filtration capacities independent of the filter cut size than the filtration trial with hydrogenated soybean oil. The capacity was only about 100 kg/m², which makes a scale up to production scale not feasible. A reason for these low capacities could be the filtration residue of the evaporated emulsion which is higher than 1% (see Table 1).

Example 4

(Embodiment of the Present Invention): Forms with Corn Oil

The emulsion was prepared as described in example 1 by using corn oil as adjuvant for dissolving β-carotene. The corn oil was purchased from Dumortier Frères, Sa 59202, Tourcoing Cedex.

The emulsion was then either filtered according to alternative a) or according to alternative b).

a) The emulsion was filtered through the 2 μm multi-layer filter ULTRAFIT® 500-P002, commercially available from LIGACON W. Röll & CO. AG (Switzerland). The achieved capacity was 500 kg/m² (see FIG. 7).

Figure 7:
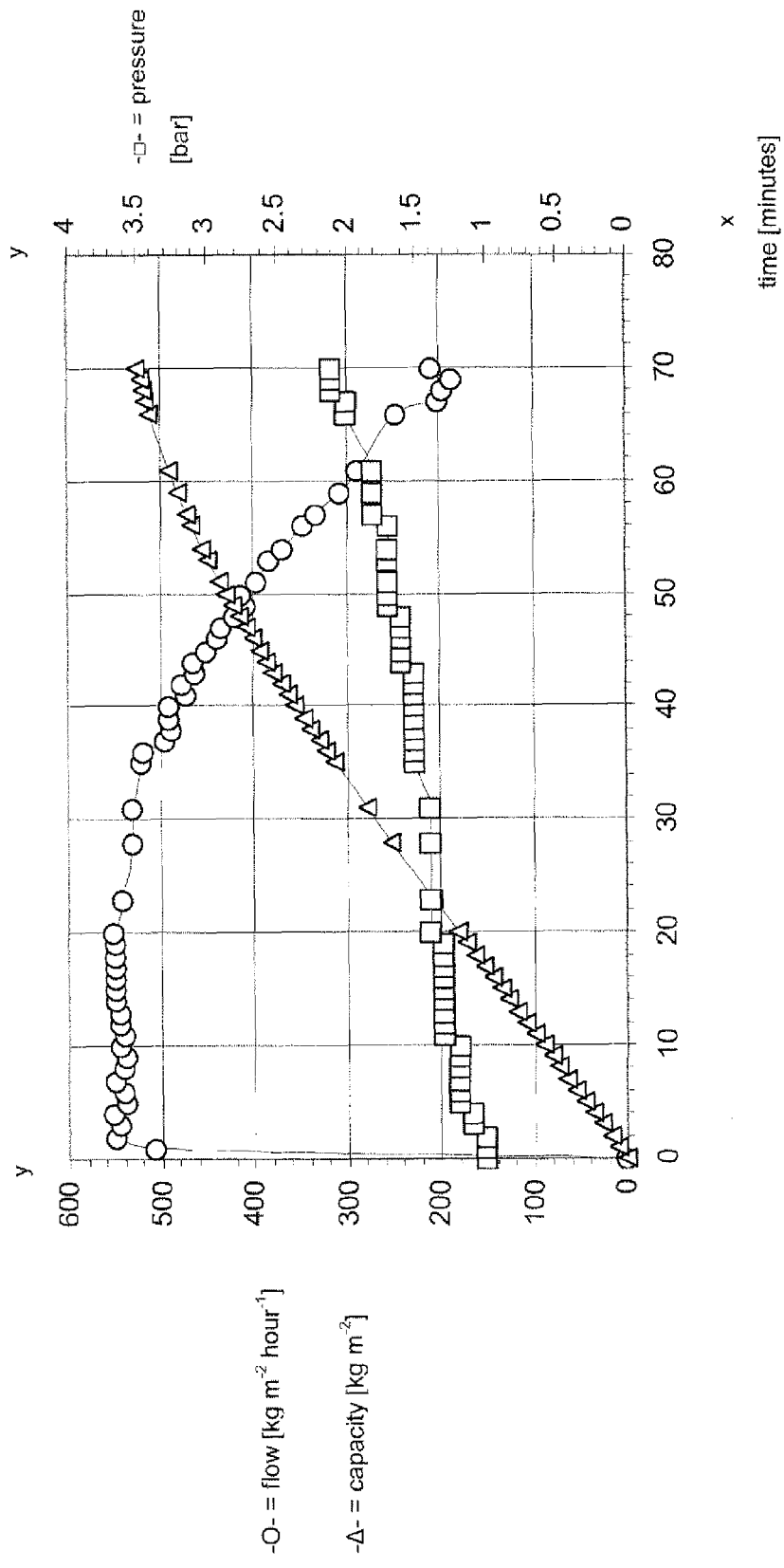
FIG. 7 shows the flow and capacity for the filtration step of corn oil with a 2 µm multilayer filter (Typ Ultrafit 500-P002).

FIG. 7 shows the flow and capacity for the filtration step of corn oil with a 2 μm multilayer filter (Typ Ultrafit 500-P002). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

b) The emulsion was filtered through the 5 μm multi-layer filter ULTRAFIT® 500-P005, commercially available from LIGACON W. Röll & CO. AG (Switzerland). The achieved capacity was 1000 kg/m² by a filtration flow of 500 kg per m² and hour (see FIG. 8).

Figure 8:
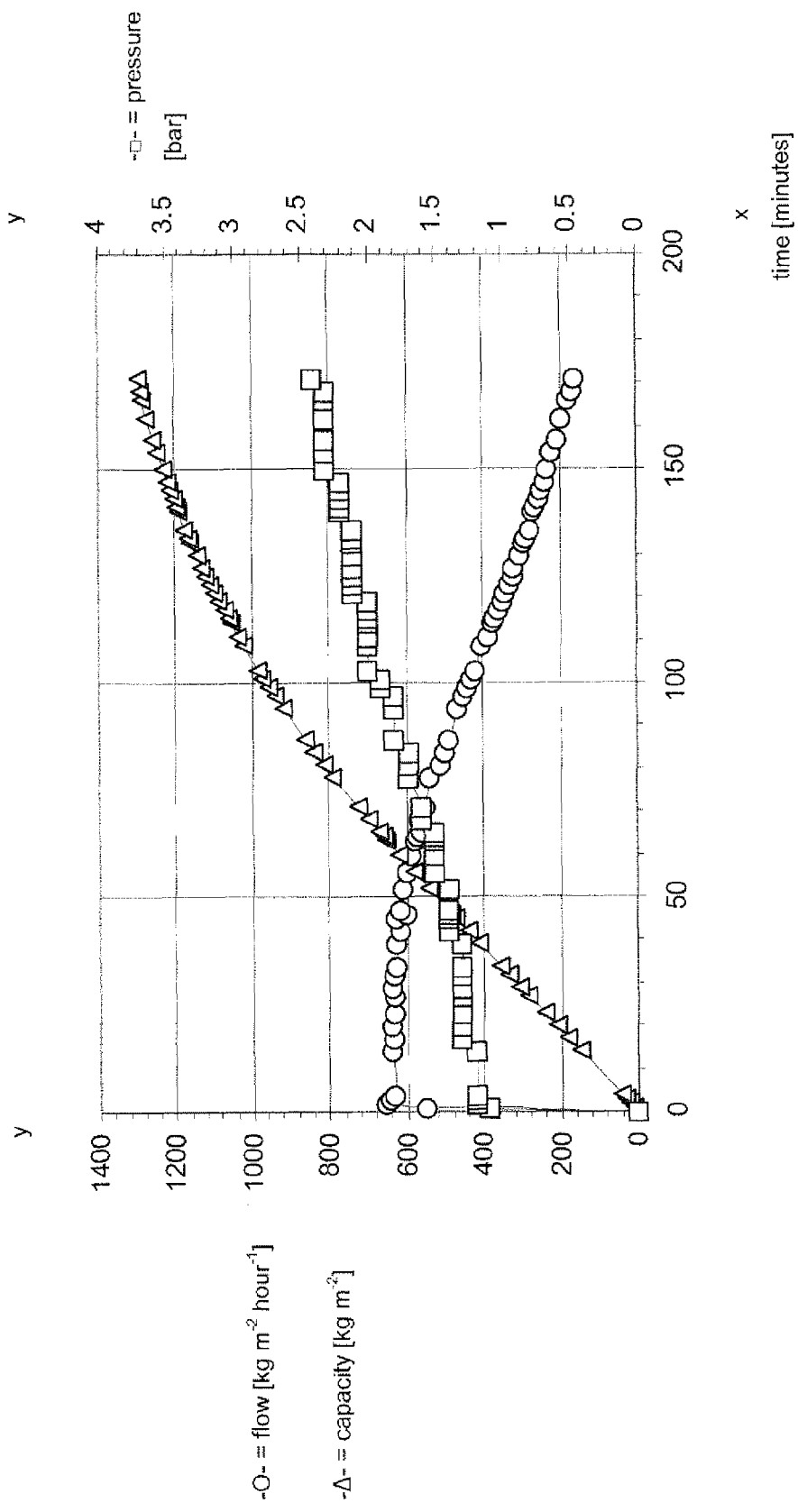
FIG. 8 shows the flow and capacity for the filtration step of hydrogenated soybean oil with a 5 µm multilayer filter (Typ Ultrafit 500-P005).

FIG. 8 shows the flow and capacity for the filtration step of hydrogenated soybean oil with a 5 μm multilayer filter (Typ Ultrafit 500-P005). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

The filtration trials a) and b) for the emulsion containing corn oil show both also a good filtration capacity.

The filtered emulsions of examples 2, 3 and 4 were converted into a solid composition by performing an additional drying step, i.e. by spray drying, spray drying or a powder catch process.

The parameters of the so-derived powders were further evaluated and are disclosed in the following table 1.

Example 5

(Embodiment of the Present Invention): Forms with Astaxathin 54 g of astaxanthin, 24 g of corn oil and 7 g of tocopherol were dissolved in methylene chloride by heating up to a temperature in the range of from 65 to 75° C. and at about 3 bar pressure resulting in a 5 weight-% solution of astaxanthin in methylene chloride.

In a separate vessel 236 g of centrifuged, spray dried HiCap®100 were dissolved/dispersed in water at 50° C. and at atmospheric pressure resulting in a 31 weight-% solution/dispersion of that starch in water.

The lipophilic phase containing astaxanthin, methylene chloride, oil and the tocopherol and the hydrophilic phase containing water and HiCap®100 were mixed together. The resulting emulsion was homogenized in the first step using rotor stator device (speed 4850 rpm) at a temperature of 65° C. In the second step the pre-emulsion is further homogenised by passing over a nozzle (diameter 200 μm) with a pressure drop of 120 bar at 67° C. Then the methylene chloride was evaporated by a cascade of two thin film evaporators at 55° C. and 497 mbar in the first evaporator and 51° C. at 72 mbar for the second evaporator.

The resulting concentrated emulsion was then filtered. The filtration trials were done by a lab-filtration tool with 0.00159 m² filter discs.

a) The emulsion was filtered through the 10 μm multi-layer filter Ultrafit 500-P010, commercially available from LIGACON W. Röll & CO. AG (Switzerland). The achieved capacity was 100 kg/m². During the short trial time no pressure increasing over filter was visible so the capacity limit was not achieved (see FIG. 9).

Figure 9:
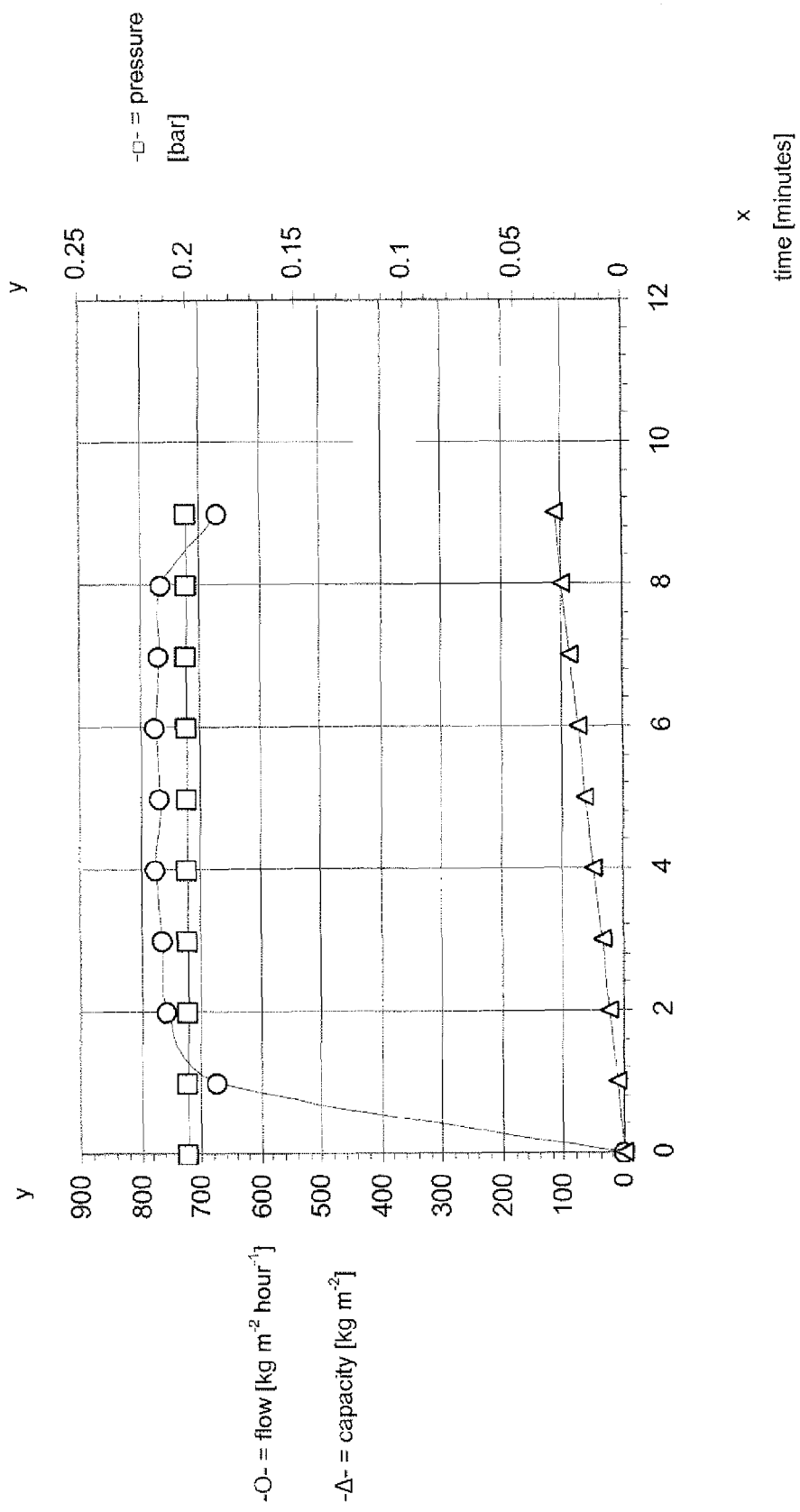
FIG. 9 shows the flow and capacity for the filtration step of corn oil with a 10 µm multilayer filter (Typ Ultrafit 500-P010).

FIG. 9 shows the flow and capacity for the filtration step of corn oil with a 10 μm multilayer filter (Typ Ultrafit 500-P010). The x-axis shows the time in minutes, the right-handed y-axis shows the pressure in bar ("-□-"), the left-handed y-axis shows the flow in kg per m² and hour ("-○-"), and the capacity in kg per m² ("-Δ-").

The invention claimed is:

1. A process for the manufacture of an emulsion or dispersion of one or more carotenoid(s) comprising the following steps:

TABLE 1

| Example | oil used in step a) | pore size of membrane [um] | particle size[1] [nm] of b-carotene in emulsion | colour intensity[2] E1/1 [—] | filtration residue[3] [weight-% based on b-carotene content] | Stocksolution test[4] |
|---|---|---|---|---|---|---|
| 2 | hydro-genated Soybean oil | 2 | 267 | 998 | 0.8 | 4.5 |
| 4 | corn oil | not filtrated | 287 | 1093 | 0.9 | 4.5 |
| 4 a) | corn oil | 2 | 273 | 1073 | 0.8 | 5.0 |
| 4 b) | corn oil | 2 | 284 | 1054 | 0.9 | 5.0 |
| 3 | hydro-genated palm oil | not filtrated | 291 | 1001 | 1.2 | 4.5 |
| 3 a) | hydro-genated palm oil | 2 | 279 | 956 | 0.7 | 5.0 |
| 3 b) | hydro-genated palm oil | 10 | 276 | 973 | 0.7 | 5.0 |
| 3 c) | hydro-genated palm oil | 25 | 282 | 956 | 0.7 | 4.5 |

The residual moisture content in all examples varied in the range of from 5.1 to 5.6 weight-%, based on the total weight of the solid form.

[1]Characteristic parameters of the particle size distribution of the inner (β-carotene) phase as measured by Photon Correlation Spectroscopy (PCS) (Coulter N4)
[2]Product form dispersed in water; measured at $\lambda(E_{max})$; baseline correction at 650 nm (20° C.)
[3]Filltration residue of β-carotene (Fitrated with paper filter pore size 7 um and filtration additive (HYFLO Super Cel))
[4]Stock solution test: Preparation of 10 wt-% powder in deionised water: The powder is dispersed with a magnetic stirrer and then kept for 12 to 18 h without agitation. After the storage ringing, floating crystals or crystal smear can appear in different characteristics. Value for the floating particles was determined.

a) dispersing one or more carotenoid(s) and one or more triglyceride(s) in water or a water-miscible or water-immiscible organic solvent selected from the group consisting of ethanol, n-propanol, iso-propanol, 1,2-butanediol-1-methylether, 1,2-propanediol-1-n-propylether, acetone, methylene chloride, dimethyl carbonate, ethyl formate, ethyl- or isopropylacetate, methyl tert-butyl ether, and mixtures thereof;

b) dissolving a modified food starch in water, wherein the concentration of the modified food starch in the so-derived aqueous matrix solution is in the range of from 20 to 50 weight-%, based on the total weight of the matrix solution;

c) separating from the solution obtained in step b) a fraction which is not soluble at atmospheric pressure in water of a temperature in the range of from 1 to 100° C.;

d) mixing the dispersion of step (a) with the solution of step (c);

e) homogenizing the thus resulting mixture of step (d);

f) removing the organic solvent if used in step (a); and g) filtrating the mixture with a multi-layer filter to separate a precipitated insoluble fraction of particles having an average particle size in the range of from 1 to 500 μm;

wherein the aqueous solution of step (b) is prepared with water of a temperature of from 1 to 30° C. and the separating step (c) is also carried out at a temperature from 1 to 30° C.

2. Process according to claim 1, wherein the carotenoid (one or more compounds) is selected from the group consisting of canthaxanthin, lycopene, β-carotene, and 8'-apo-β-carotenal.

3. Process according to claim 1, wherein the carotenoid is β-carotene.

4. Process according to claim 1, wherein the triglyceride (one or more compounds) is selected from the group consisting of corn oil, sunflower oil, (hydrogenated) soybean oil, and (hydrogenated) palm oil.

5. Process according to claim 1 wherein the modified food starch is starch sodium octenyl succinate (OSA).

6. Process according to claim 1 further comprising an additional drying step (h) wherein the emulsion or dispersion obtainable in step (g) is converted into a solid composition (solid form).

7. A process for the manufacture of an emulsion or dispersion of β-carotene comprising the following steps:

a) dispersing one or more carotenoid(s) comprising β-carotene and one or more triglyceride(s) in a solvent selected from the group consisting of water or a water-miscible or water-immiscible organic solvent selected from the group consisting of ethanol, n-propanol, iso-propanol, 1,2-butanediol-1-methylether, 1,2-propanediol-1-n-propylether, acetone, methylene chloride, dimethyl carbonate, ethyl formate, ethyl- or isopropylacetate, methyl tert-butyl ether, and mixtures thereof;

b) dissolving modified food starch in water, wherein the concentration of the modified food starch in the so-derived aqueous matrix solution is in the range of from 20 to 50 weight-%, based on the total weight of the matrix solution;

c) separating from the solution obtained in step (b) a fraction which is not soluble at atmospheric pressure in water of a temperature in the range of from 1 to 100° C.;

d) mixing the dispersion of step (a) with the solution of step (c);

e) homogenizing the thus resulting mixture of step (d);

f) removing the organic solvent if used in step (a); and g) filtrating the mixture with a multi-layer filter to separate a precipitated insoluble fraction of particles having an average particle size in the range of from 1 to 500 μm;

wherein the aqueous solution of step (b) is prepared with water of a temperature of from 1 to 30° C. and the separating step (c) is also carried out at a temperature from 1 to 30° C.

* * * * *